US008130971B2

(12) United States Patent
Werner

(10) Patent No.: US 8,130,971 B2
(45) Date of Patent: Mar. 6, 2012

(54) MANUALLY SWITCHING DUAL-MODE HEARING PROTECTOR

(76) Inventor: Theodore J. Werner, Huntington Station, NY (US)

( * ) Notice: Subject to any disclaimer, the term of this patent is extended or adjusted under 35 U.S.C. 154(b) by 1178 days.

(21) Appl. No.: 11/586,242

(22) Filed: Oct. 25, 2006

(65) Prior Publication Data

US 2007/0154027 A1 Jul. 5, 2007

Related U.S. Application Data

(60) Provisional application No. 60/756,002, filed on Jan. 4, 2006.

(51) Int. Cl.
*A61F 11/06* (2006.01)

(52) U.S. Cl. ........... 381/72; 381/73.1; 381/74; 381/23.1

(58) Field of Classification Search ................. 381/23.1, 381/72, 73.1, 74, 77, 55, 56, 71.14, 312, 381/60
See application file for complete search history.

(56) References Cited

U.S. PATENT DOCUMENTS

| | | | | |
|---|---|---|---|---|
| 2002/0080979 | A1* | 6/2002 | Brimhall et al. | 381/72 |
| 2005/0105755 | A1* | 5/2005 | Yueh | 381/371 |
| 2006/0140416 | A1* | 6/2006 | Berg | 381/72 |

* cited by examiner

*Primary Examiner* — Vivian Chin
*Assistant Examiner* — Leshui Zhang
(74) *Attorney, Agent, or Firm* — Charles E. Baxley

(57) ABSTRACT

A manually switching dual-mode hearing protector including an active hearing protection device that does not only provide for acoustic attenuation of ambient sound in order to protect hearing of a user in a noisy environment but in addition provides electro-acoustically bypassing of this acoustic attenuation function in order to provide the user with a communication function in order to enable the user to perceive speech signals even when wearing the manually switching dual-mode hearing protector in a noisy environment.

6 Claims, 4 Drawing Sheets

MANUALLY SWITCHING DUAL-MODE HEARING PROTECTOR

1. CROSS REFERENCE TO RELATED APPLICATIONS

The instant non-provisional patent application claims priority from provisional patent application No. 60/756,002, filed on Jan. 4, 2006, and entitled HEARING PROTECTOR WITH ALTERNATE NOISE CLIPPING SHUT OFF SYSTEM AND COMPRESSION NOISE FILTERING SYSTEM, and incorporates it herein by reference thereto.

2. BACKGROUND OF THE INVENTION

A. Field of the Invention

The embodiments of the present invention relate to a dual-mode hearing protector, and more particularly, the embodiments of the present invention relate to a manually switching dual-mode hearing protector.

B. Description of the Prior Art

A large part of the population is exposed to hazardous noise from time to time. This can be at work, while traveling, during leisure activities, or at home. The exposure can lead to permanent hearing loss, distract people's attention from other hazards, or simply cause stress.

In order to prevent both accidents and permanent hearing damage, hearing protection devices ("HPDs") have been provided in many styles and over many years. It started with the earmuff that is still very relevant and addresses very noisy environments, e.g., airports, construction, shooting, or complex working/communication situations, e.g., fighter pilots.

Over the years, development of biocompatible soft materials has enabled soft earplugs in different styles and colors, as well as recent development of "one fits many" standard semi-soft earplugs in silicon-rubber type materials. For severe situations, the combination of an earmuff and an "in-the-ear" HPD is required to achieve desired attenuation. The physical limitation of hearing protection based on ear worn devices is defined where bone-conduction—body acoustics—becomes dominant at around 40 dB attenuation.

The in-the-ear styles mentioned are devices made to fit "the average" ear in one way or the other. Either the fit is provided by softness of the material leading to undefined device insertion and undefined attenuation, or the fit is provided by standard shaped structures intended to block off the ear canal. In both cases, the flat distribution of the individual shape of the outer ear and the ear canal leads to a bad fit, pressure points in the ear, and undefined positioning of the device.

To address this wearing comfort issue, in-the-ear hearing aid technology has been applied making customized ear molds with passive acoustical filter. These are long lasting devices with good wearing comfort. This customization process, however, is traditionally a very manual process creating varying results over time, low reproducibility, and the quality is very operator-skill dependent.

Customized earplugs are earplugs including a hard shell having an outer surface individually shaped according to the measured inner shape of the user's outer ear and ear canal. These earplugs presently are primarily used for housing hearing aids. The inner shape of the user's outer ear and ear canal may be measured, for example, by direct laser scanning or by forming an impression. The customized hard shell may be produced by an additive process, such as layer-by-layer laser sintering of a powder material.

On the other hand, soft earplugs are widely used, in particular also as hearing protection devices. A soft earplug has an outer surface with a standardized shape, and is made of a relatively soft material so that the outer surface of the earplug is capable of adapting its shape to the individual inner shape of the user's outer ear and ear canal.

It is commonly known to design hearing protection devices as so-called active hearing protection devices wherein each device is provided with an outer microphone for converting ambient sound into input audio signals, a signal processing unit for processing the input audio signals into output audio signals, and an acoustic output transducer, i.e., a speaker or receiver, converting the audio output signals into sound perceivable by the user when wearing the hearing protection device. Thereby the hearing protection device is provided with a communication function enabling the user to perceive ambient sound signals in a controlled manner even when wearing the hearing protection device in a noisy environment.

In order to provide for a selective communication function, i.e., in order to enable the user to perceive, for example, speech while suppressing undesired noise, it is known to provide the audio signal processing unit with the capability of assessing the sound picture and adapting filter and gain settings to the noise level dynamically.

Numerous innovations for hearing protection earphones have been provided in the prior art that will be described below, which are in chronological order to show advancement in the art, and which are incorporated herein by reference thereto. Even though these innovations may be suitable for the specific individual purposes to which they address, they each differ in structure, and/or operation, and/or purpose from the embodiments of the present invention in that they do not teach a manually switching dual-mode hearing protector.

(1) U.S. Pat. No. 5,355,418 to Kelsey et al.

U.S. Pat. No. 5,355,418 issued to Kelsey et al. on Oct. 11, 1994 in class 381 and subclass 72 teaches a frequency selective hearing protection device and method utilizing adaptive filtering to hinder transmission of frequency components in ambient sound above a preselected threshold level. Sound frequency components not above the threshold level, such as normal speech, are allowed to pass. Electrical analog signals produced by a transducer are converted to a stream of digital input signals. The digital input signals are applied to a digital filter, such as an FIR filter, implementing a time domain difference equation. As a result, digital output signals are produced, which are reconverted to analog output signals and applied to an actuator to produce audible sound. To adjust the frequency response to suppress gain at frequency components above the threshold, windows of input and output data signals are first assembled. Respective frequency domain transforms, such as fast Fourier transforms, provide spectrums representative of frequency component amplitudes. Any violator components exceeding the threshold level are distinguished and coefficient values of the difference equation are altered to suppress gain at those frequencies. Preferably, the coefficient values are readjusted to again allow the frequencies to pass if the threshold is not exceeded in a preselected number of subsequent digital input signals.

(2) U.S. Pat. No. 5,361,304 to Jones et al.

U.S. Pat. No. 5,361,304 issued to Jones et al. on Nov. 1, 1994 in class 381 and subclass 72 teaches a headphone assembly for an active noise cancellation system, having a rigid molded plastics shell with a rigid baffle dividing the shell interior into a front volume and a closed rear volume, both of which may be filled with an acoustic foam. The baffle has a central opening in which is mounted a headphone transducer. A seal cushion is disposed around the mouth of the shell to effect an air-tight seal against the user's head. The headphone transducer has two effective sound-radiating surfaces of different sizes, and may be constructed as a form of orthodynamic drive unit. In the latter case, the orthodynamic drive unit diaphragm may have two separate coils of different radial extents.

(3) United States Patent Application Publication Number 2001/0046304 to Rast.

United States Patent Application Publication Number 2001/0046304 published to Rast on Nov. 29, 2001 in class 381 and subclass 74 teaches an apparatus and method for providing controlled acoustic isolation within various forms of headsets. Manual and automatic mechanisms change the amount of acoustic isolation provided by the headsets. Sounds in the environment that the user wishes to be made aware of can be programmed into a set of stored sound selection characteristics. In response to correlation of the stored sound characteristics with sounds in the external environment, the headset decreases acoustic isolation by coupling signals from one or more external microphones to the audio conversion elements within the earpieces. Alternatively, the apparatus can respond to sounds to be blocked by increasing acoustic isolation. A manual control may be activated by the user to decrease acoustic isolation at their discretion.

(4) U.S. Pat. No. 6,801,629 to Brimhall et al.

U.S. Pat. No. 6,801,629 issued to Brimhall et al. on Oct. 5, 2004 in class 381 and subclass 72 teaches a noise attenuating system, including a core portion adapted to actively filter sound waves into various bands and passing only those bands corresponding to safe amplitude sounds to a wearer's ear canal. Unlike conventional active noise cancellation systems, active noise attenuation is accomplished without providing additional sound waves inversely to unsafe amplitude sound waves. Instead, unsafe amplitude sound waves are passively blocked and only safe amplitude sound waves are passed through to the wearer's ear canal.

(5) United States Patent Application Publication Number 2006/0045299 to Haussmann.

United States Patent Application Publication Number 2006/0045299 published to Haussmann on Mar. 2, 2006 in class 381 and subclass 328 teaches a hearing protection earplug, including a shell for being worn at least in part in the ear canal of a user. The shell has a sound passage extending from an outer sound inlet opening of the shell to an inner sound output opening adapted to acoustically connect to the user's ear canal. A noise attenuation button is provided at the outer end of the shell and is manually movable relative to the shell between a resting position in which the outer sound inlet opening of the shell is closed by the button and at least one communication position in which the outer sound inlet opening of the shell is at least partially opened by the button for enabling sound communication between the environment and the sound passage of the shell. The sound passage is designed so that it has a sound attenuation of less than 10 dB averaged over the audible frequencies. Also taught is a use of the earplug and a method for manufacturing the earplug.

(6) United States Patent Application Publication Number 2006/0140416 to Berg.

United States Patent Application Publication Number 2006/0140416 published to Berg on Jun. 29, 2006 in class 381 and subclass 72 teaches a hearing protection system, including a first and a second hearing protection device. Each hearing protection device includes an active unit including an acoustic input transducer for converting ambient sound into input audio signals and an acoustic output transducer for transforming filtered audio signals into sound perceivable by the user. At least one of the active units include an audio signal processing unit for processing the input audio signals into the filtered audio signals. The audio signal processing unit includes an analyzer module for determining the intensity of the input audio signals separately for a plurality of spectral classes, a judgement module for judging—depending on the determined spectral intensities of the input digital audio signals—which one of a plurality of predetermined criteria is presently fulfilled by the input audio signals, and a filter module having adaptive frequency and time domain filter settings—depending on the judgement made by said judgement module—for producing the filtered audio signals. The judgement module is adapted to detect close speech. The filter settings are selected by the judgement module so that the filter settings provide for a transparent mode if the judgement module judges that no noise is present, for a first attenuation mode if the judgement module judges that noise without close speech is present, and for a second attenuation mode if the judgement module judges that noise with close speech is present.

It is apparent that numerous innovations for hearing protection earphones have been provided in the prior art that are adapted to be used. Furthermore, even though these innovations may be suitable for the specific individual purposes to which they address, they would not be suitable for the purposes of the embodiments of the present invention as heretofore described, namely, a manually switching dual-mode hearing protector.

3. SUMMARY OF THE INVENTION

Thus, an object of the embodiments of the present invention is to provide a manually switching dual-mode hearing protector that avoids the disadvantages of the prior art.

Briefly stated, another object of the present invention is to provide a manually switching dual-mode hearing protector including an active hearing protection device that does not only provide for acoustic attenuation of ambient sound in order to protect hearing of a user in a noisy environment, but in addition provides electro-acoustically bypassing of this acoustic attenuation function in order to provide the user with a communication function in order to enable the user to perceive speech signals even when wearing the manually switching dual-mode hearing protector in a noisy environment.

The novel features considered characteristic of the embodiments of the present invention are set forth in the appended claims. The embodiments of the present invention themselves, however, both as to their construction and to their method of operation together with additional objects and advantages thereof will be best understood from the following description of the specific embodiments when read and understood in connection with the accompanying drawing.

4. BRIEF DESCRIPTION OF THE DRAWINGS

The figures of the drawings are briefly described as follows.

5. LIST OF REFERENCE NUMERALS UTILIZED IN DRAWINGS

Figure 1:
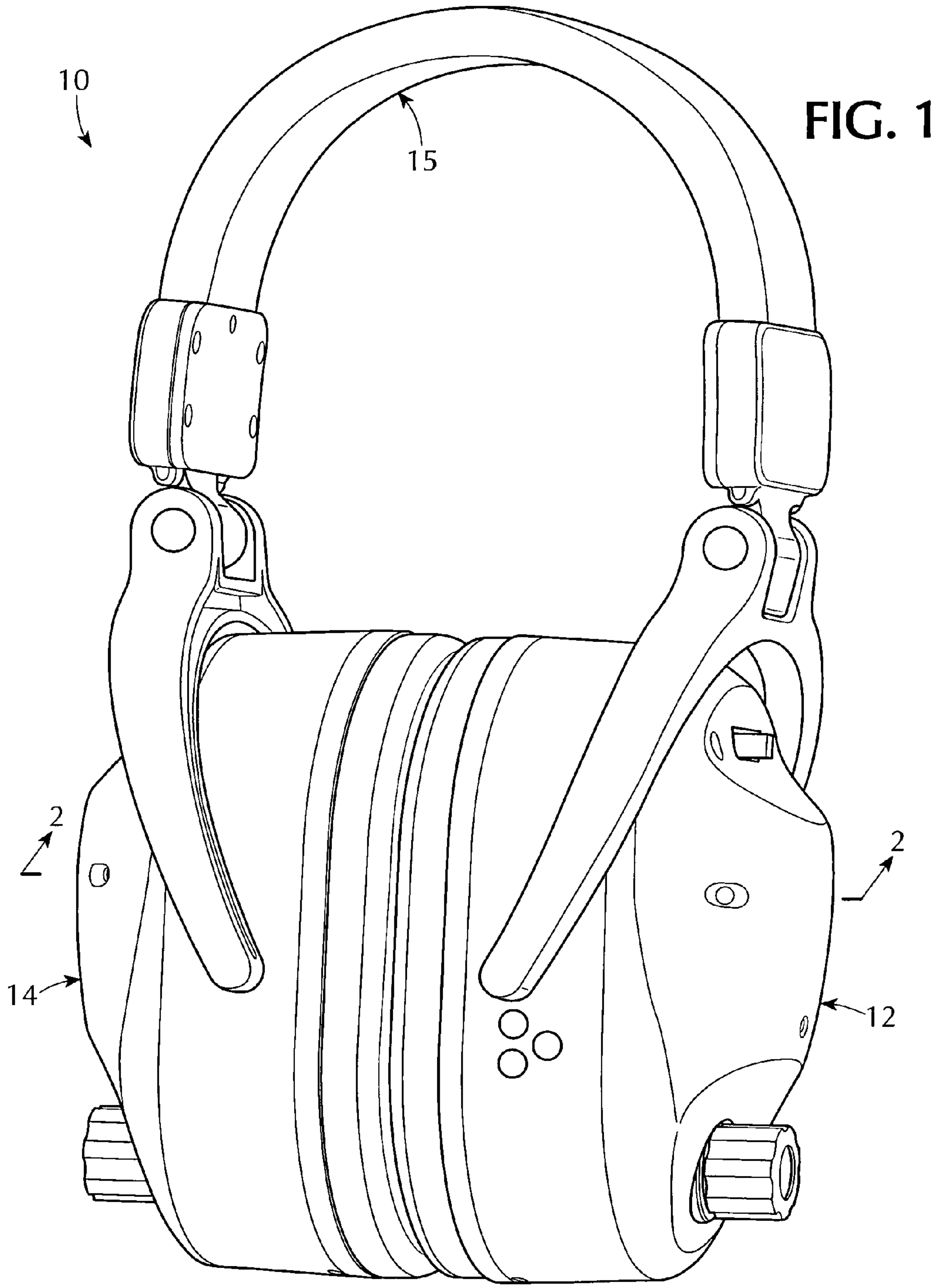
FIG. 1 is a diagrammatic perspective view of the manually switching dual-mode hearing protector of the embodiments of the present invention.

A. General.

10 manually switching dual-mode hearing protector of embodiments of present invention B. Manually Switching Dual-Mode Hearing Protector 10.

12 right cup for covering right ear of user

14 left cup for covering left ear of user

15 band for wearing over top of head of user

16 active unit of each of right cup 12 and left cup 14

18 microphone of active unit 16 of each of right cup 12 and left cup 14 for converting ambient sound impinging on associated one of right cup 12 and left cup 14 into input audio signals

20 audio signal processing unit of active unit 16 of each of right cup 12 and left cup 14 for processing input audio signals provided by microphone 18 of active unit 16 of associated one of right cup 12 and left cup 14 into filtered audio signals

22 acoustic output transducer of active unit 16 of each of right cup 12 and left cup 14 for converting filtered audio signals provided by audio signal processing unit 20 of active unit 16 of associated one of right cup 12 and left cup 14 into sound that is perceivable by user's ear

23 battery interface of active unit 16 of each of right cup 12 and left cup 14 for interfacing with battery 25 for powering manually switched dual-mode hearing protector 10

24 interface of audio signal processing unit 20 of active unit 16 of each of right cup 12 and left cup 14 for temporarily connecting with remote unit via wireless or wired data connection for uploading programs and data into audio signal processing unit 20 of active unit 16 of associated one of right cup 12 and left cup 14

25 battery for powering manually switched dual-mode hearing protector 10

26 compression filtering circuit of audio signal processing unit 20 of active unit 16 of each of right cup 12 and left cup 14

28 clipping shut off circuit of audio signal processing unit 20 of active unit 16 of each of right cup 12 and left cup 14

30 manually operated switch of audio signal processing unit 20 of active unit 16 of each of right cup 12 and left cup 14

6. DETAILED DESCRIPTION OF THE PREFERRED EMBODIMENTS

A. General

Referring now to the figures, in which like numerals indicate like parts, and particularly to FIG. 1, which is a diagrammatic perspective view of the manually switching dual-mode hearing protector of the embodiments of the present invention, the manually switching dual-mode hearing protector of the embodiments of the present invention is shown generally at 10.

The manually switching dual-mode hearing protector 10 is an active hearing protection devices, e.g., a hearing protection device that does not only provide for acoustic attenuation of ambient sound in order to protect hearing of a user in a noisy environment, i.e., "clipping shut off", but in addition provides electro-acoustically bypassing of this acoustic attenuation function in order to provide the user with a communication function, e.g., in order to enable the user to perceive speech signals even when wearing the manually switching dual-mode hearing protector 10 in a noisy environment, i.e., "compression filtering."

B. The Manually Switching Dual-Mode Hearing Protector 10

The manually switching dual-mode hearing protector 10 comprises a right cup 12 for covering the right ear of the user, a left cup 14 for covering the left ear of the user, and a band 15 connecting the right cup 12 to the left cup 14 and for wearing over the top of the head of the user.

Figure 2:
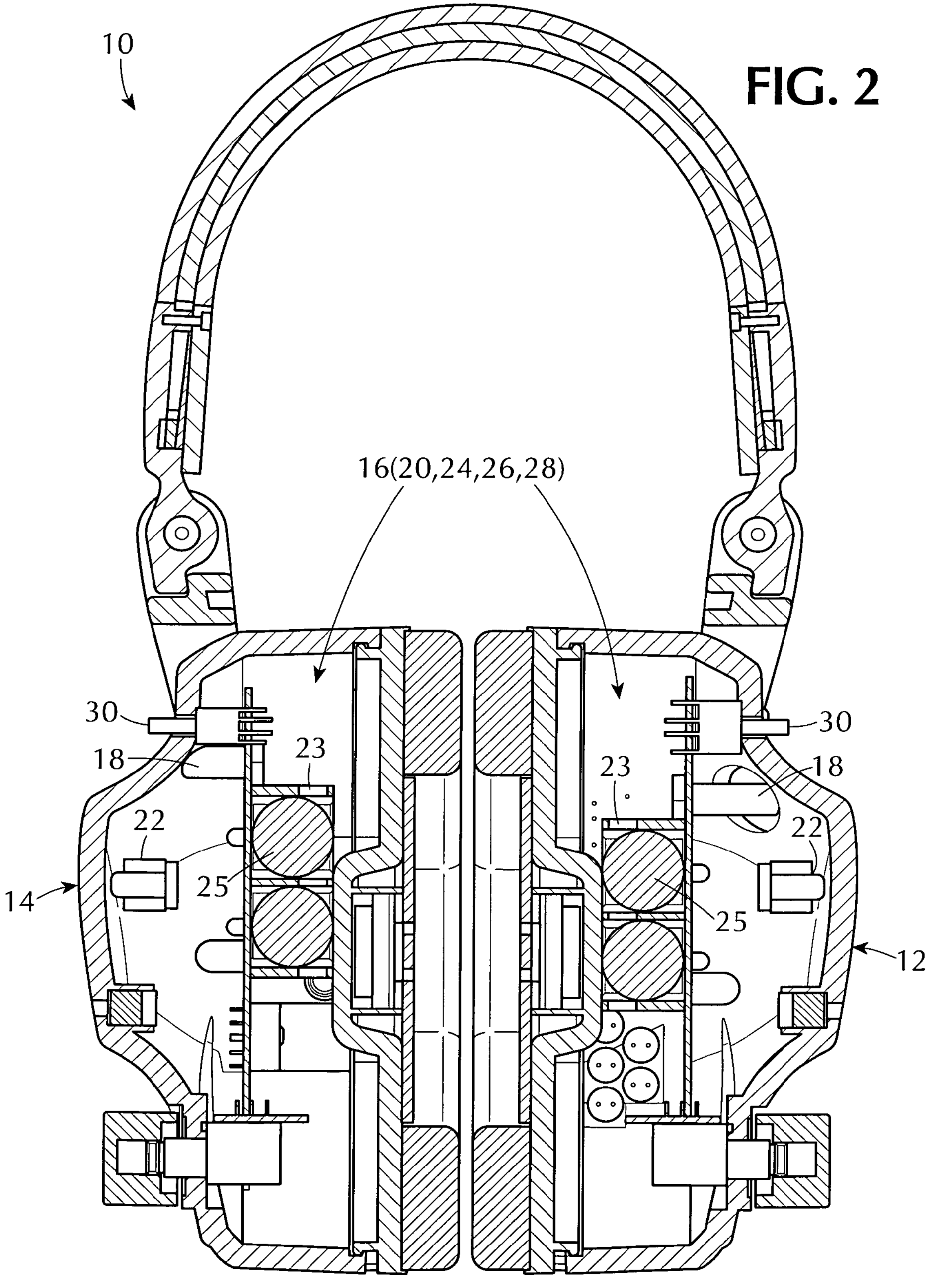
FIG. 2 is a diagrammatic cross sectional view taken along LINE 2-2 in FIG. 1 illustrating the right circuitry of the right cup of the manually switching dual-mode hearing protector of the embodiments of the present invention and the left circuitry of the left cup of the manually switching dual-mode hearing protector of the embodiments of the present invention.
Figure 3:
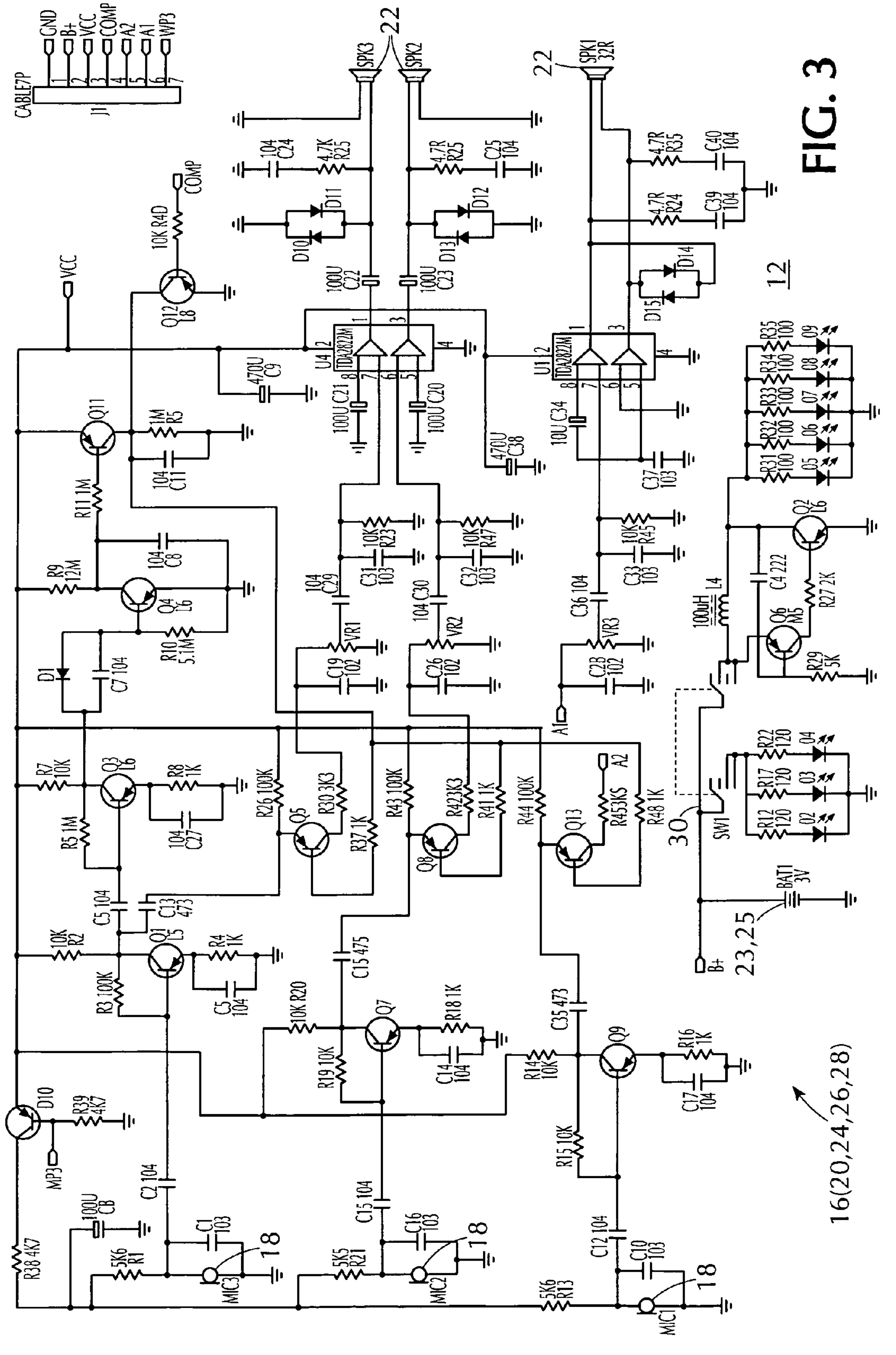
FIG. 3 is a schematic diagram of the right circuit of the right cup of the manually switching dual-mode hearing protector of the embodiments of the present invention.
Figure 4:
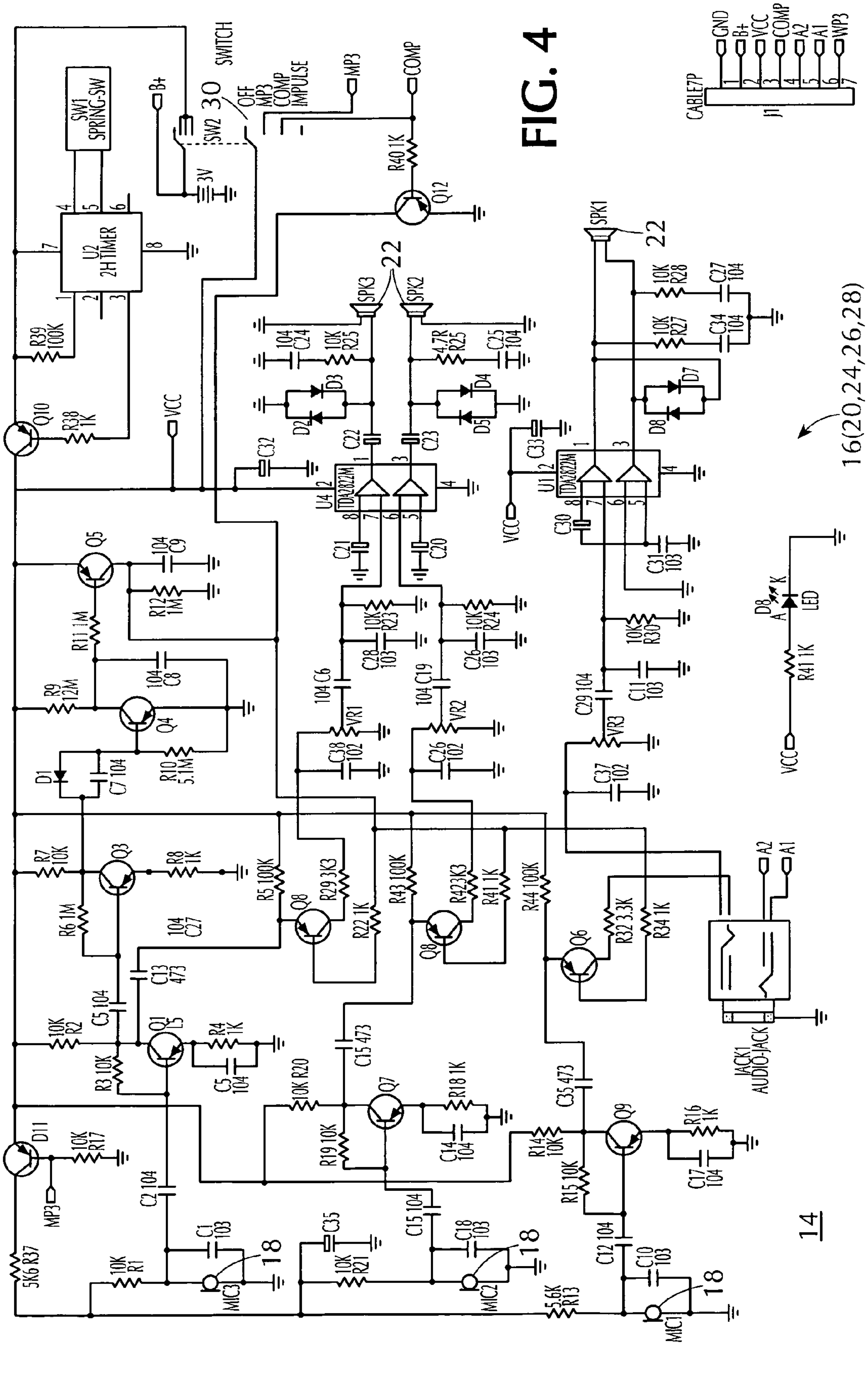
FIG. 4 is a schematic diagram of the left circuit of the left cup of the manually switching dual-mode hearing protector of the embodiments of the present invention.

As shown in FIGS. 2-4, which are, respectively, a diagrammatic cross sectional view taken along LINE 2-2 in FIG. 1 illustrating the right circuitry of the right cup of the manually switching dual-mode hearing protector of the embodiments of the present invention and the left circuitry of the left cup of the manually switching dual-mode hearing protector of the embodiments of the present invention, a schematic diagram of the right circuit of the right cup of the manually switching dual-mode hearing protector of the embodiments of the present invention, and a schematic diagram of the left circuit of the left cup of the manually switching dual-mode hearing protector of the embodiments of the present invention, the manually switching dual-mode hearing protector 10 further comprises each of the right cup 12 and the left cup 14 having an active unit 16.

The active unit 16 of each of the right cup 12 and the left cup 14 comprises a microphone 18, an audio signal processing unit 20, an acoustic output transducer 22, and a battery interface 23 for interfacing with a battery 25 for powering the manually switched dual-mode hearing protector 10.

The microphone 18 of the active unit 16 of each of the right cup 12 and the left cup 14 is for converting ambient sound impinging on an associated one of the right cup 12 and the left cup 14 into input audio signals.

The audio signal processing unit 20 of the active unit 16 of each of the right cup 12 and the left cup 14 is for processing the input audio signals provided by the microphone 18 of the active unit 16 of an associated one of the right cup 12 and the left cup 14 into filtered audio signals.

The acoustic output transducer 22 of the active unit 16 of each of the right cup 12 and the left cup 14 is for converting the filtered audio signals provided by the audio signal processing unit 20 of the active unit 16 of an associated one of the right cup 12 and the left cup 14 into sound that is perceivable by an associated ear of the user, e.g., a speaker.

The audio signal processing unit 20 of the active unit 16 of each of the right cup 12 and the left cup 14 is a digital signal processor including a memory for storing programs and data.

Thus, the active unit 16 of each of the right cup 12 and the left cup 14 in addition comprises an analogue-to-digital converter between the microphone 18 of the active unit 16 of each of the right cup 12 and the left cup 14 and the audio signal processing unit 20 of the active unit 16 of an associated one of the right cup 12 and the left cup 14 and a digital-to-analogue converter between the audio signal processing unit 20 of the active unit 16 of the associated one of the right cup 12 and the left cup 14 and the acoustic output transducer 22 of the active unit 16 of the associated one of the right cup 12 and the left cup 14.

The audio signal processing unit 20 of the active unit 16 of each of the right cup 12 and the left cup 14 further comprises an interface 24 for temporarily connecting with a remote unit via a wireless or wired data connection for uploading programs and data into the audio signal processing unit 20 of the active unit 16 of an associated one of the right cup 12 and the left cup 14, i.e., a program/data memory. These data may include user specific audio data, such as an existing hearing loss, in order to individually configure the audio signal processing unit for optimizing performance.

The audio signal processing unit 20 of the active unit 16 of each of the right cup 12 and the left cup 14 is designed to enable, on the one hand, selective perception of desired sound signals, such as speech signals, both in low noise and high noise environments, i.e., "compression filtering", while on the other hand, protection of hearing of the user from excessive ambient sound levels is ensured, i.e., "clipping shut off".

To this end, the audio signal processing unit 20 of the active unit 16 of each of the right cup 12 and the left cup 14 further comprises a compression filtering circuit 26, a clipping shut off circuit 28, and a manually operated switch 30.

The manually operated switch 30 of the audio signal processing unit 20 of the active unit 16 of each of the right cup 12 and the left cup 14 selectively switches between the compression filtering circuit 42 of the audio signal processing unit 20 of the active unit 16 of an associated one of the right cup 12 and the left cup 14 when the user desires compression filtering and the clipping shut off circuit 28 of the audio signal processing unit 20 of the active unit 16 of the associated one of the right cup 12 and the left cup 14 when the user desires clipping shut off.

C. Conclusions

It will be understood that each of the elements described above or two or more together may also find a useful application in other types of constructions differing from the types described above.

While the embodiments of the present invention have been illustrated and described as embodied in a manually switching dual-mode hearing protector, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis the foregoing will so fully reveal the gist of the embodiments of the present invention that others can by applying current knowledge readily adapt it for various applications without omitting features that from the standpoint of prior art fairly constitute characteristics of the generic or specific aspects of the embodiments of the present invention.

The invention claimed is:

1. A manually switching dual-mode hearing protector, comprising an active hearing protection device;

wherein said active hearing protection device does not only have an acoustic attenuation function to provide for acoustic attenuation of ambient sound in order to protect hearing of a user in a noisy environment and thereby provide clipping shut off, but in addition provides electro-acoustically bypassing of said acoustic attenuation function in order to provide the user with a communication function in order to enable the user to perceive speech signals even when wearing said manually switching dual-mode hearing protector in a noisy environment and thereby provide compression filtering;

wherein said active hearing protection device comprises a right cup;

wherein said right cup is for covering the right ear of the user;

wherein said active hearing protection device comprises a left cup;

wherein said left cup is for covering the left ear of the user;

wherein each of said right cup and said left cup has an active unit;

wherein said active unit of each of said right cup and said left cup comprises an audio signal processing unit;

wherein said audio signal processing unit of said active unit of each of said right cup and said left cup comprises a manually operated switch;

wherein said manually operated switch of said audio signal processing unit of said active unit of each of said right cup and said left cup provides selective electronic switching between a compression filtering circuit of said audio signal processing unit of said active unit of an associated one of said right cup and said left cup when the user desires compression filtering and a clipping shut off circuit of said audio signal processing unit of said active unit of said associated one of said right cup and said left cup when the user desires clipping shut off;

wherein said active unit of each of said right cup and said left cup comprises a microphone;

wherein said active unit of each of said right cup and said left cup comprises an acoustic output transducer;

wherein said active unit of each of said right cup and said left cup comprises a battery interface;

wherein said battery interface of said active unit of each of said right cup and said left cup is for interfacing with a battery;

wherein said battery is for powering said manually switched dual-mode hearing protector;

wherein said audio signal processing unit of said active unit of each of said right cup and said left cup is a digital signal processor;

wherein said digital signal processor of said audio signal processing unit of said active unit of each of said right cup and said left cup includes a memory;

wherein said memory of said digital signal processor of said audio signal processing unit of said active unit of each of said right cup and said left cup is for storing programs and data;

wherein said active unit of each of said right cup and said left cup comprises an analogue-to-digital converter;

wherein said analogue-to-digital converter of said active unit of each of said right cup and said left cup is between said microphone of said active unit of an associated one of said right cup and said left cup and said audio signal processing unit of said active unit of said associated one of said right cup and said left cup;

wherein said active unit of each of said right cup and said left cup comprises a digital-to-analogue converter;

wherein said digital-to-analogue converter of said active unit of each of said right cup and said left cup is between said audio signal processing unit of said active unit of an associated one of said right cup and said left cup and said acoustic output transducer of said active unit of said associated one of said right cup and said left cup;

wherein said audio signal processing unit of said active unit of each of said right cup and said left cup comprises an interface;

wherein said interface of said audio signal processing unit of said active unit of each of said right cup and said left cup is for temporarily connecting with a remote unit via a wireless or wired data connection for uploading programs and data into said audio signal processing unit of said active unit of an associated one of said right cup and said left cup; and wherein said data uploaded into said audio signal processing unit of said active unit of each of said right cup and said left cup includes user specific audio data to individually configure said audio signal processing unit of said active unit of an associated one of said right cup and said left cup for optimizing performance.

2. The protector of claim 1, wherein said active hearing protection device comprises a band;

wherein said band connects said right cup to said left cup; and wherein said band is for wearing over the top of the head of the user.

3. The protector of claim 1, wherein said microphone of said active unit of each of said right cup and said left cup is for converting ambient sound impinging on an associated one of said right cup and said left cup into input audio signals;

wherein said audio signal processing unit of said active unit of an associated one of said right cup and said left cup is for processing said input audio signals provided by said microphone of said active unit of said associated one of said right cup and said left cup into filtered audio signals; and wherein said acoustic output transducer of said active unit of said associated one of said right cup and said left cup is for converting said filtered audio signals provided by said audio signal processing unit of said active unit of said associated one of said right cup and said left cup into sound that is perceivable by an associated ear of the user.

4. The protector of claim 1, wherein said audio signal processing unit of said active unit of each of said right cup and said left cup does not only have said acoustic attenuation function to provide for acoustic attenuation of ambient sound in order to protect hearing of the user in a noisy environment and thereby provide clipping shut off, but in addition provides electro-acoustically bypassing said acoustic attenuation function in order to provide the user with said communication function in order to enable the user to perceive speech signals even when wearing said manually switching dual-mode hearing protector in a noisy environment and thereby provide compression filtering.

5. The protector of claim 1, wherein said audio signal processing unit of said active unit of each of said right cup and said left cup comprises a compression filtering circuit; and wherein said audio signal processing unit of said active unit of each of said right cup and said left cup comprises a clipping shut off circuit.

6. The protector of claim 1, wherein said acoustic output transducer of said active unit of each of said right cup and said left cup is a speaker.

* * * * *